United States Patent
Wuebbe

(10) Patent No.: US 10,004,426 B2
(45) Date of Patent: Jun. 26, 2018

(54) METHOD AND IMAGING APPARATUS FOR POSITIONING A PATIENT SLICE FROM WHICH IMAGE DATA ARE TO BE ACQUIRED

(71) Applicant: Siemens Aktiengesellschaft, Munich (DE)

(72) Inventor: Marcus Wuebbe, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 325 days.

(21) Appl. No.: 14/736,707

(22) Filed: Jun. 11, 2015

(65) Prior Publication Data
US 2015/0359453 A1 Dec. 17, 2015

(30) Foreign Application Priority Data
Jun. 11, 2014 (DE) .......................... 10 2014 211 130

(51) Int. Cl.
| | | |
|---|---|---|
| *A61B 5/05* | (2006.01) | |
| *A61B 5/055* | (2006.01) | |
| *G01R 33/483* | (2006.01) | |
| *G01R 33/54* | (2006.01) | |

(52) U.S. Cl.
CPC ........ A61B 5/0555 (2013.01); G01R 33/4833 (2013.01); G01R 33/543 (2013.01); *A61B 2560/0475* (2013.01); *A61B 2576/00* (2013.01); *G01R 33/546* (2013.01)

(58) Field of Classification Search
CPC .......................... A61B 5/0555; A61B 5/4528
See application file for complete search history.

(56) References Cited

U.S. PATENT DOCUMENTS

| | | |
|---|---|---|
| 6,792,066 B1 | 9/2004 | Harder et al. |
| 8,831,703 B2 | 9/2014 | van der Kouwe et al. |
| 2005/0088177 A1 | 4/2005 | Schreck et al. |
| 2013/0165767 A1 | 6/2013 | Darrow et al. |

FOREIGN PATENT DOCUMENTS

| | | |
|---|---|---|
| CN | 102908142 A | 2/2013 |
| JP | 2009279218 A | 12/2009 |
| JP | 2012231822 A | 11/2012 |

OTHER PUBLICATIONS

Bauer et al.; "Automatic Scan Planning for Magnetic Resonance Imaging of the Knee Joint"; Annals of Biomedical Engineering; vol. 40; pp. pp. 2033-2042 (2012).

*Primary Examiner* — Hien Nguyen
(74) *Attorney, Agent, or Firm* — Schiff Hardin LLP

(57) ABSTRACT

In a method for slice positioning of an examination subject in a magnetic resonance system an item of localization information describing the arrangement of the examination subject is automatically determined at least one item of alignment information is automatically determined. At least one slice positioning entry is acquired by an operator, which includes a selection of one of the items of alignment information or an item of manual positioning information. Offset information, which includes a relative slice positioning effected by the manual positioning information, is automatically determined and the slice positioning is determined as a function of the slice positioning entries and the offset information. The offset information is stored separately from the slice positioning in a magnetic resonance measurement protocol, and is used in a further configuration of a further slice positioning.

8 Claims, 5 Drawing Sheets

FIG 3
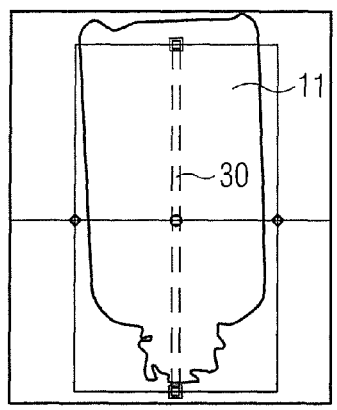
FIG 4
| Slice group | 1 | Initial Position | Isocenter |
|---|---|---|---|
| Position | Isocenter | L | 0.0 mm |
| Orientation | Sagittal | P | 0.0 mm |
| Phase enc. dir. | A>>P | H | 0.0 mm |
| AutoAlign | Head>Basis | Initial Orientation | Sagittal |
| | | Initial Rotation | 0.00 deg |
FIG 5
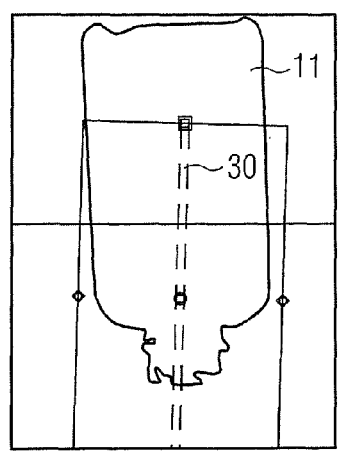

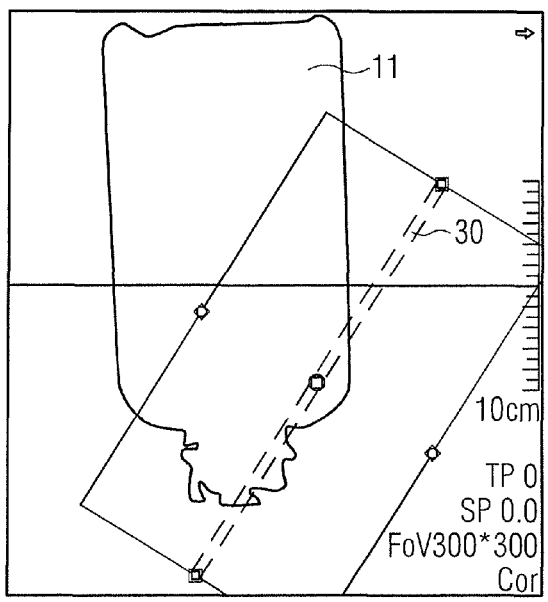

| | | |
|---|---|---|
| Slice group | 1 | Initial Position L42.0 P7.0 H43.3 |
| Position | L42.0 P7.0 F43.3 | L 42.0 mm |
| Orientation | S>T32.4>C-0.4 | P 7.0 mm |
| Phase enc. dir. | A>>P | H 43.3 mm |
| AutoAlign | — | Initial Orientation S>T |
| | | 32.4 |
| | | >C -0.4 |
| | | Initial Rotation 1.28 deg |

METHOD AND IMAGING APPARATUS FOR POSITIONING A PATIENT SLICE FROM WHICH IMAGE DATA ARE TO BE ACQUIRED

BACKGROUND OF THE INVENTION

Field of the Invention

The present invention relates to a method for positioning a slice of a person being examined in a magnetic resonance examination, wherein the slice positioning can take place using automatic alignment information and manual positioning information. The invention further relates to a magnetic resonance apparatus designed to implement such a method.

Description of the Prior Art

Automatic slice positioning in an imaging examination, in particular in magnetic resonance (MR) examinations, is used to simplify the positioning of the person being examined in, for instance, a magnetic resonance system. The automatic slice positioning is also referred to as auto-align function. Once localization information has been determined, for instance with the use of a so-called localizer algorithm, corresponding information required for positioning can be determined, with the use of the automatic slice positioning, such as in the form of matrices, in order to acquire an MR data record from certain organs or regions of the person being examined. This information is stored in the system and, based on a selection by a user, the auto-align function can access this information and automatically position the slice to be measured at the suitable position with the use of the information. Manual positioning by a person operating the magnetic resonance system thus is not needed, because the apparatus itself shifts the slices to the desired position.

The operator, however, often is not entirely satisfied with the automatically determined position and adds, for instance, an additional translation or rotation thereto. The changed position is then stored in a magnetic resonance measurement protocol. If it is used again, the magnetic resonance measurement protocol thus will acquire MR data again precisely at the desired position.

The manual additional translation or rotation performed by the operator/technician usually has a similar effect on the slice positioning as the automatic slice positioning by means of the auto-align function. If, for instance, a magnetic resonance measurement protocol is used that was produced by an automatic slice positioning and an additional manual translation or rotation, the resulting slice positioning is now known. Then, if the magnetic resonance protocol is reused and an automatic slice positioning is applied again, for instance with the use of the auto-align function, the slice positioning is shifted again in accordance with the auto-align function. This, however, does not result in the desired slice positioning, because the starting point was already used by the first automatic slice positioning.

SUMMARY OF THE INVENTION

An object of the present invention is to improve the conventional methods for slice positioning.

According to the present invention, in a method for positioning a slice of a person being examined for a magnetic resonance examination in a magnetic resonance system, localization information, that represents an arrangement of the person being examined in the magnetic resonance system with respect to a reference position, is automatically determined. The reference position can include, for example, the position of the isocenter in the magnetic resonance system. The determination of the localization information can be performed with a so-called localizer function, in which the person being examined, together with an examination bed, is continuously moved through several bed positions, and magnetic resonance recordings (data acquisition) are continuously acquired with a reduced resolution compared with the subsequent diagnostic magnetic resonance images. Alignment information is automatically determined on the basis of the localization information. Each of the several alignment functions is assigned to a respectively determined examination region of the person being examined. For instance, alignment information can be assigned to an organ or a region of the body. For instance, alignment information can be assigned to the head, the heart, a kidney or a foot of the person being examined. Each item of alignment information includes a corresponding item of positioning information, which includes a slice positioning that is suited to the respective examination region. The positioning information may include, for instance, a matrix of geometric translations and rotations for the slice positioning. For instance, alignment information, which is assigned to the head of the person being examined, may include a relative translation that specifies a displacement of the patient starting from the reference position, in order to move the head of the patient into the isocenter of the magnetic resonance system. Further translations in the right/left direction or anterior/posterior direction may be constituents of the alignment information, such as for alignment with an eye or an ear of the person being examined. Different rotations of the slice to be recorded may similarly be useful for certain organs or body parts. The thus determined alignment information can subsequently be used for an automatic slice positioning with the use of the auto-align function described in the introduction to the description.

Via a user interface of the magnetic resonance system, for example, at least one slice positioning entry is made by a person operating the magnetic resonance system. The operator can select one of the items of alignment information for the slice positioning entry and, alternatively or in addition, can enter a manual item of positioning information. The manual positioning information may be entered, for instance, as a numerical value or a numerical value change in a corresponding entry window of the user interface. The manual positioning information may include for instance relative or absolute geometric translations and/or rotations for the slice positioning. Alternatively or in addition, the manual positioning information can be provided in a graphical representation on the user interface by moving and/or rotating a slice currently selected for the slice positioning. For instance, a magnetic resonance image of the person being examined from the localization information can be selected in a graphical representation for instance and the currently selected slice positioning can be shown based on that image.

This slice positioning, which is shown for instance by geometric forms such as rectangles or lines in the graphical representation, can be changed by moving or rotating the geometric forms with, for instance, a computer mouse or a touch-sensitive screen. At the same time, changes to the slice positioning effected in the graphical representation due to the movement or rotation can be represented and updated in corresponding display fields on the user interface in the form of numerical values. The slice positioning thus can be set both by selecting one of the items of alignment information and by the manual positioning. With the method, offset information is also automatically determined as a function of the at least one acquired slice positioning entry, wherein the offset information includes a relative slice positioning effected by the manual positioning information with respect to the determined reference position. In other words, it is determined in the offset information, which will also be referred to in the subsequent description as offset, how the slice positioning was influenced on the basis of the manual positioning information, i.e. regardless of selected alignment information that was selected by the auto-align function. Furthermore, the slice positioning is automatically determined as a function of the slice positioning entries. The offset information is then saved in a magnetic resonance measurement protocol separately from the slice positioning. The magnetic resonance measurement protocol can be used during an implementation of the magnetic resonance examination to automatically actuate the magnetic resonance system. Furthermore, the offset information can be used in a further configuration of a further slice positioning.

For instance, a first slice positioning can be configured, by the operator selecting an item of alignment information, for a head recording for instance, and correcting this by a few centimeters by acquiring an additional item of manual positioning information. The correction determined from the manual positioning information is stored as offset information separately from the resulting slice positioning in for instance the magnetic resonance measurement protocol. In a further slice positioning, the selection information is for instance selected by the operator for a shoulder of the person being examined. On account of the separately stored offset information, a slice positioning can automatically take place as a function of the alignment information and the offset information assigned to the shoulder so that an additional entry of the correction is not required.

In an embodiment, the offset information can be displayed on a user interface of the magnetic resonance system, for instance the translations defined by the offset information in each of the three spatial directions and rotations in each of the three spatial directions can be displayed for instance as numerical values. With a manual correction of the slice positioning in for instance a graphical representation of the person being examined, the numerical values can be automatically adapted to the offset information. As a result, a user of the magnetic resonance system is shown in a simple manner how the current slice positioning is composed of alignment information and offset information.

According to the present invention, a magnetic resonance system is also provided, which includes a basic field magnet, a gradient field system, a radio-frequency antenna and a control facility.

The control facility, which can include for instance a gradient controller, a radio-frequency controller and an image sequence controller, is used for instance to actuate the gradient field system and the radio-frequency antenna, to receive measurement signals received by the radio-frequency antenna, to evaluate the measurement signals and to produce magnetic resonance tomography images. The magnetic resonance system further includes a positioning apparatus for configuring a slice positioning of a person being examined for a magnetic resonance examination in the magnetic resonance system. Furthermore, the magnetic resonance system includes a movable examination couch with an examination couch control apparatus. A magnetic resonance examination of a person being examined arranged on the examination couch can be performed for instance with a magnetic resonance measurement protocol, which includes information relating to the slice positioning and image control, i.e. the magnetic resonance measurement protocol includes information for controlling the radio-frequency controller, the gradient controller, the image sequence controller and the couch controller. The positioning apparatus is configured to automatically determine localization information, which provides for an arrangement of the person being examined in the magnetic resonance system in respect of a certain reference position, and to automatically determine at least one item of alignment information on the basis of the localization information. A respective item of alignment information is assigned to a respective certain examination region of the person being examined, for instance an organ or a body part. The respective alignment information includes positioning information for a slice positioning, which is suited to the respective examination region assigned to the alignment information. The positioning apparatus is also able to acquire at least one slice positioning entry from an operator of the magnetic resonance system. A respective slice positioning entry here includes a selection of one of the items of alignment information or an acquisition of an item of manual positioning information. Offset information is automatically determined as a function of the acquired slice positioning entries, which offset information includes a relative slice positioning affected only by the manual positioning information in respect of the determined reference position. As a function of the at least one slice positioning entry and the offset information, the positioning apparatus automatically determines the slice positioning. In the event that no manual positioning information was entered by the operator, the offset information can be set to zero for instance in each spatial direction and in each spatial rotational direction. The offset information is then saved by the positioning apparatus in the magnetic resonance measurement protocol separately from the slice positioning. The magnetic resonance measurement protocol can be used during the implementation of the magnetic resonance examination to automatically actuate the magnetic resonance system to perform the magnetic resonance examination. The positioning apparatus further uses the offset information in a further configuration of a further slice positioning, in which for instance another item of alignment information is selected, for instance another organ or another body part.

The magnetic resonance system is thus suited to implementing the previously described method and its embodiments and therefore also includes the advantages described above in conjunction with the method.

The present invention, a non-transitory storage medium encoded with programming instructions (code), which can be loaded into a memory of a programmable control facility of a magnetic resonance system. The programming instructions cause all or various previously described embodiments of the inventive method to be executed. The programming instructions may require other program means, e.g. libraries or auxiliary functions, in order to realize the embodiments of the method. The code may be a source code e.g. C++, which must still be compiled and translated and linked or which only has to be interpreted, or an executable software code, which for execution purposes only has to be loaded into the corresponding control facility.

The electronically readable data carrier can be, for instance a DVD, a magnetic tape or a USB stick, on which electronically readable control information, in particular software, is stored.

BRIEF DESCRIPTION OF THE DRAWINGS

FIGS. 3, 5, 6 and 9 show graphical representations of an examination object and a slice positioning according to an embodiment of the present invention.

FIGS. 4, 7 and 8 show entry masks of a positioning apparatus according to an embodiment of the present invention.

DESCRIPTION OF THE PREFERRED EMBODIMENTS

Figure 1:
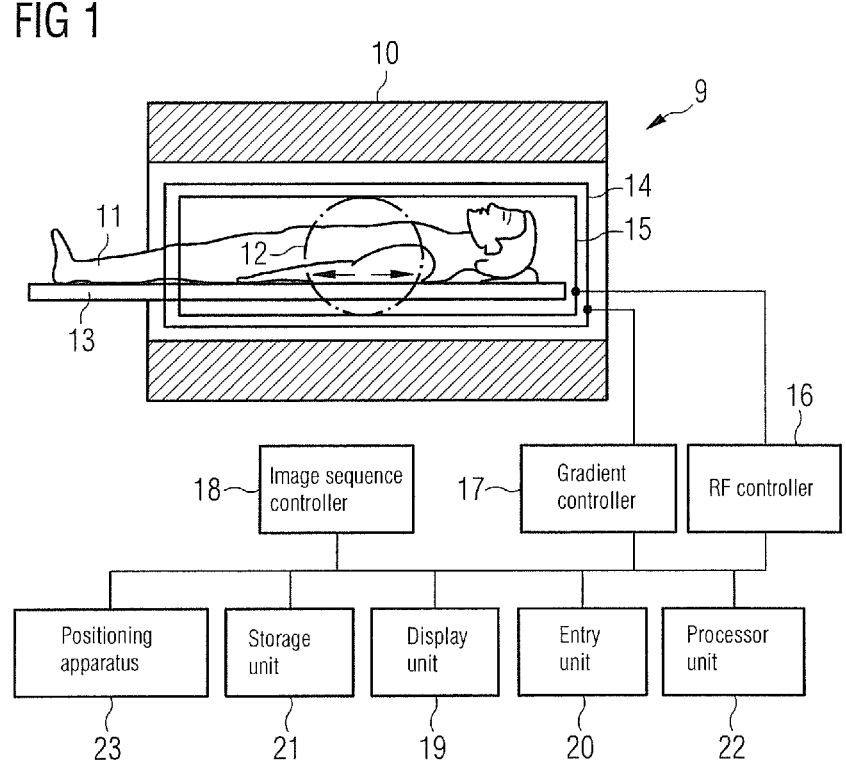
FIG. 1 schematically shows a magnetic resonance system according to an embodiment of the present invention.

FIG. 1 shows a schematic representation of a magnetic resonance system 9, which is designed to record (acquire) magnetic resonance signals. A magnetic resonance system 9 of this type has a scanner with a basic field magnet 10 for generating a basic magnetic field B0. An examination object, for instance a person being examined 11, is moved into the basic field magnet 10, in order to record magnetic resonance signals of the person being examined 11 in an examination region 12. The person being examined 11 can herewith lie on an automatically movable couch 13. The scanner of the magnetic resonance system 9 further has a gradient apparatus 14 for generating magnetic field gradients. For the excitation of nuclear spins to give them a magnetization that deviates from the B0 field, a radio-frequency apparatus 15 is provided in the scanner, which can radiate a radio-frequency field into the person being examined 11 so as to deflect the magnetization out of the position of equilibrium. A radio-frequency controller 16 is provided for controlling the radio-frequency coils of the radio-frequency apparatus 15. A gradient controller 17 is provided to control the magnetic field gradient. An image sequence controller 18 is provided, which controls a sequence of irradiated radio-frequency pulses and magnetic field gradients as a function of the selected image recording sequence and which thus also controls the radio-frequency controller 16 and the gradient controller 17. Magnetic resonance images can be shown on a display unit 19, or an operator can plan a measurement, by specifying the imaging volume on the display unit 19 by way of an entry unit 20 for instance. Predetermined imaging sequences or other programs, which are required to operate the magnetic resonance system 9, can be stored in a storage unit 21 for instance. The magnetic resonance system 9 further includes a positioning apparatus 23, which assists the operator with a slice positioning. The operating principle of the positioning apparatus 23 is then described in detail with reference to FIGS. 2-9. A central processor unit 22 can control the magnetic resonance system 9. The basic operating principles of a magnetic resonance system 9 is known to those skilled in the art, and thus need not explained in more detail here.

The components shown in FIG. 1 as different units do not have to be realized in the separation of units shown. The individual units can also be combined, by means of hardware, software or a combination of hardware and software.

Figure 2:
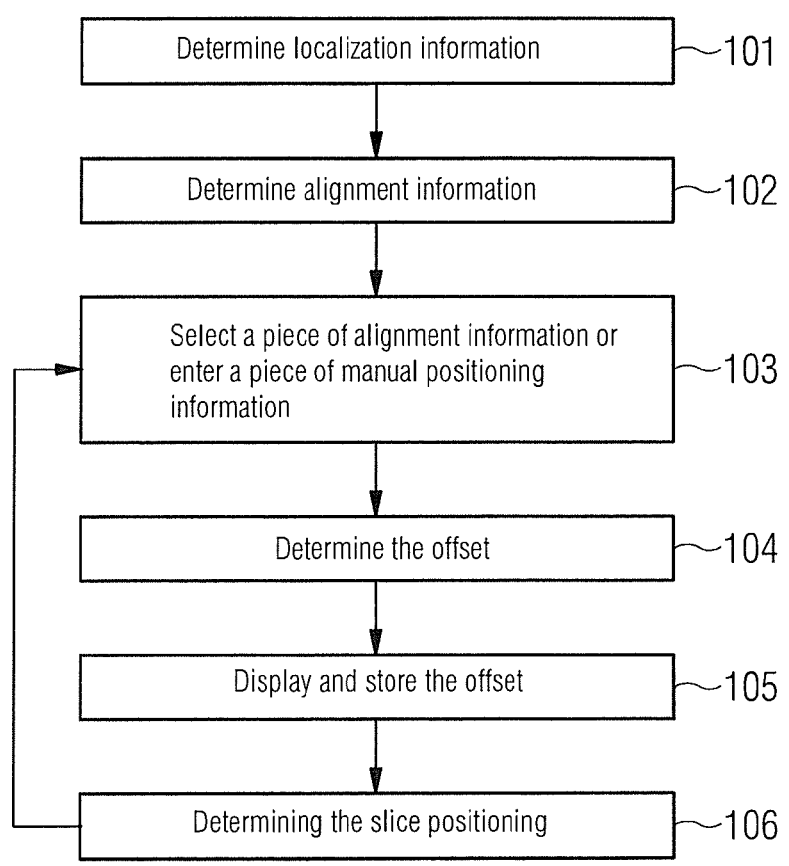
FIG. 2 shows a flowchart with the basic steps for configuring a slice positioning according to an embodiment of the present invention.
Figures 8, 9:
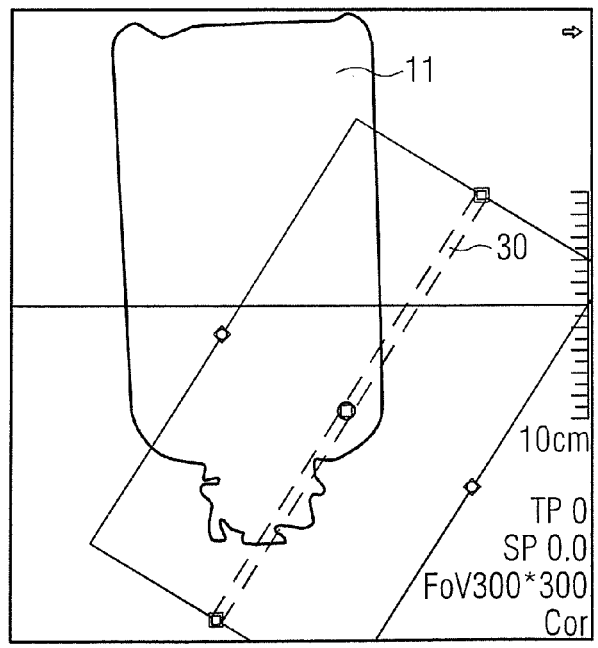

The operation of the positioning apparatus 23 is described in detail below with reference to FIGS. 2-9. FIG. 2 shows a sequence of method steps 101-106 and FIGS. 3, 5, 6 and 9 show graphical representations of an examination object on for instance the display unit 19 of the magnetic resonance system 9, and FIGS. 4, 7 and 8 show entry masks which can be shown for instance on the display unit 19 of the magnetic resonance system 9. In FIGS. 3, 5, 6 and 9, the examination object is referred to with reference character 11. In FIGS. 3, 5, 6 and 9, a bottle-shaped phantom was used as the examination object instead of a person being examined. A current slice 30 selected by the slice positioning is marked in FIGS. 3, 5, 6 and 9 by two dashed lines.

A number of parameters are shown on a graphical surface in FIGS. 4, 7, and 8, of which the parameters relevant to this description are then explained in brief. The parameter "position" specifies the current position of the slice selected for the slice positioning. In FIG. 4, this is for instance the isocenter of the magnetic resonance system 9 and in FIGS. 7 and 8 the position specifies translations in spatial directions in millimeters, wherein the following abbreviations are used: L for a translation to the left, R for a translation to the right, P for a translation to the rear (posterior), A for a translation to the front (anterior), H for a translation in the direction of the head (head) and F for a translation in the direction of the feet (feet). The field "orientation" specifies the cutting direction of the slice selected by way of the slice positioning, for instance sagittal, transversal or coronal or a combination thereof, wherein rotations are referred to as angles in the corresponding body planes with the abbreviations S for sagittal, T for transversal and C for coronal. In the "auto-align" field, an automatic slice positioning can be set with regards to an organ or body part of the body, for instance the head can be selected as the base (head>base). If no automatic slice positioning is selected, this field contains a dash such as e.g. in FIG. 8. In the "initial position" field, an item of offset information described below, a so-called offset, is shown using the same representational scheme as in the afore-described field "position". The individual components of the field "initial position" for the three spatial directions can be set by a user in the fields shown therebelow, namely for the spatial directions right/left in the first field below the field "initial position", for the spatial direction anterior/posterior in the second field blow the field "initial position" and for the spatial direction head/foot in the third field below the field "initial position". The field "initial orientation" shows the current alignment of the slice selected for the slice positioning as compared with the afore-described field "orientation". If the slice positioning by the user includes a rotation of the slice in a number of spatial directions, these can be set in the three fields below the field "initial orientation" for the directions, sagittal, transversal and coronal.

With the display unit 19, the method for configuring a slice positioning shown in FIG. 2 is implemented in the positioning apparatus 23. In step 101, localization information of the examination object 11 is determined for instance with a so-called localizer. A number of items of alignment information are determined in step 102, which, in each instance, store information required accordingly for the positioning as matrices in for instance the storage unit 21, in order to record certain organs of for instance a person being examined. In the example of the phantom 11 in FIG. 3, an item of alignment information of this type may include for instance information as a matrix, in order for instance to position the bottle head of the bottle-shaped phantom 11 for a magnetic resonance recording in a suitable manner in the magnetic resonance system 9. A so-called auto-align function can access this alignment information and automatically position the slice to be measured, with the aid of the matrix, at the corresponding position.

FIG. 3 shows an example of the phantom 11 with a slice positioning in the basic state. With the slice positioning in this basic state, MR data from a slice of the phantom 11 are acquired, which, in the basic state of the system, is in the isocenter of the system 9. By actuating the field "auto-align" in FIG. 4, a user selects for instance an automatic slice positioning for the head (step 103 in FIG. 2). As a result, as shown in FIG. 5, the slice 30 to be measured is moved in the direction of the head of the phantom object 11. Since no manual slice positioning was implemented, but instead only the automatic positioning via the "auto-align" selection, the values of the current offset or the current offset information are neutral, as shown in FIG. 4. The user can now also enter an item of manual positioning information (step 103), for instance by the user displacing and rotating the slice 30 to be measured in the graphical representation in FIG. 5 with for instance a computer mouse or with the use of a touchscreen at the display unit 19, for instance into the position shown in FIG. 6. FIG. 7 shows the parameters resulting therefrom for the position and alignment of the slice to be measured in the fields "position" and "orientation". In addition, offset information effected by the manual user entry into the fields "initial position" and "initial orientation" and the fields for the translations into the spatial directions and the rotations into the spatial directions lying therebelow is determined and displayed (step 104).

The position of the slice to be measured, which is shown in the field "position", is thus produced from the "initial position", which was effected by the user interaction and the matrix of the auto-align function of the head (head>base). Similarly, the alignment of the slice to be measured is produced, which is shown in the field (orientation), from the alignment change "initial orientation" effected by the user interaction and the alignment based on the auto-align function. In step 105, the offset information is also stored in for instance a magnetic resonance measurement protocol. The entire resulting slice positioning is determined in step 106 and is shown in the fields "position" and "orientation". The method is continued in step 103, whereupon the user selects for instance another matrix of the auto-align function, for instance for a foot of the phantom object 11. Since the offset information was also stored, a new slice positioning can be used by taking the offset information and the positioning information of the matrix in step 106 into account for a new determination of the slice positioning. Alternatively or in addition, the user can introduce a further item of manual positioning information in step 103, whereby the offset information is changed, which is determined in step 104 and the changed offset information is stored in step 105 in the magnetic resonance measurement protocol.

Due to the representation of the entire resulting position of the current slice positioning in the fields "position" and "orientation" and the displays of the currently selected auto-align function in the field "auto-align" and the used offset information in the fields "initial position" and "initial orientation", the user obtains a transparent item of information as to how the current slice positioning is made up.

A similar slice positioning can be achieved for instance by purely manual slice positioning entries, therefore without using an auto-align function, as shown in the example of FIG. 8. In this case, the user has not activated the auto-align function, but has instead set a slice positioning for instance via the graphical user interface or by changing the fields on the right side under "initial position" and "initial orientation". This is directly reflected in the fields "position" and "orientation", since no additional auto-align function is active. This slice position is shown graphically in FIG. 9.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for positioning a slice within an object from magnetic resonance (MR) data are to be acquired with an MR apparatus comprising an MR scanner, said method comprising:

using a processor to operate said MR scanner in order to execute a localization scan of the object;

in said processor, automatically determining localization information from said localization scan that describes an arrangement of the object in the MR scanner with respect to a reference position;

in said processor, executing an auto-align function algorithm in order to automatically determine at least one item of alignment information from the localization information, with positioning information being individually assigned by the processor to a respective examination region of the object, with each item of alignment information comprising an item of positioning information for a slice in the respective examination region;

manually making at least one slice positioning entry into said processor that includes an item of manual positioning information describing a manual positioning of the object in the MR scanner;

in said processor, automatically determining offset information dependent on said at least one slice positioning entry, said offset information including a relative slice positioning of said slice effected only by said manual positioning information, with respect to said reference position;

in said processor, automatically determining a position of the object in the MR scanner dependent on said at least one slice positioning entry and said offset information in order to operate the MR scanner to place the slice at the determined position and to acquire MR data from the slice at the determine position;

using said processor to operate said MR scanner in order to obtain an MR image of the slice at the determined position, and making the MR image of the slice at the determined position available in electronic from the processor, as a data file;

electronically storing the offset information separately from the determined positioning of the object, in a magnetic resonance measurement protocol in a form that is retrievable to automatically operate the MR scanner, using the magnetic resonance measurement protocol, to acquire said MR data from said slice;

in a different acquisition of MR data for a different slice in the object, separately retrieving the offset information and using the retrieved offset information to configure a different slice position for said different slice in said different MR data acquisition, and to operate the MR scanner to obtain an MR image of said different slice at said different slice position; and making said MR image of said different slice available from said processor in electronic form, as a further data file.

2. A method as claimed in claim 1 comprising displaying said offset information at a user interface in communication with said processor.

3. A method as claimed in claim 1 comprising generating said positioning information as a matrix of geometric movements, selected from the group consisting of translations and rotations.

4. A method as claimed in claim 1 comprising designating said manual positioning information in said at least one slice positioning entry by, via a user interface in communication with said processor, at least one of:
    setting numerical values for relative geometric movements of said slice, selected from the group consisting of consisting of translations and rotations; and
    displaying a representation of the slice to be positioned in a displayed representational image of the object, and displacing the representation of said slice with respect to the displayed representational image.

5. A method as claimed in claim 1 wherein said examination object is a person, and comprising selecting said examination region to include a predetermined organ of the person.

6. A method as claimed in claim 1 comprising in said at least one manual slice positioning entry, also selecting one of the items of alignment information from a displayed list of said items of alignment information.

7. A magnetic resonance (MR) apparatus comprising:
    an MR scanner;
    a processor configured to operate said MR scanner in order to execute a localization scan of an object;
    said processor being configured to automatically determine localization information from said localization scan that describes an arrangement of the object in the MR scanner with respect to a reference position;
    said processor being configured to execute an auto-align function algorithm in order to automatically determine at least one item of alignment information from the localization information, with positioning information being individually assigned by the processor to a respective examination region of the object, with each item of alignment information comprising an item of positioning information for a slice in the respective examination region;
    said processor having an interface that receives at least one slice positioning entry into said processor that includes an item of manual positioning information describing a manual positioning of the object in the MR scanner;
    said processor being configured to automatically determine offset information dependent on said at least one slice positioning entry, said offset information including a relative slice positioning of said slice effected only by said manual positioning information, with respect to said reference position;
    said processor being configured to automatically determine a position of the object in the MR scanner dependent on said at least one slice positioning entry and said offset information in order to operate the MR scanner to place the slice at the determined position and to acquire MR data from the slice at the determined position;
    said processor being configured to operate said MR scanner in order to obtain an MR image of the slice at the determined position, and making the MR image of the slice at the determined position available in electronic from the processor, as a data file;
    a memory;
    said processor being configured to store the offset information separately from the determined position of the object, in a magnetic resonance measurement protocol in said memory in a form that is retrievable to automatically operate the MR scanner, using the magnetic resonance measurement protocol, to acquire said MR data from said slice;
    in a different acquisition of MR data for a different slice in the object, said processor being configured to separately retrieve the offset information from the memory and using the retrieved offset information to set, a different slice position for said different slice in said different MR data acquisition, and to operate the MR scanner to obtain an MR image of said different slice at said different slice position; and
    said processor being configured to make said MR image of said different slice available from said processor in electronic form, as a further data file.

8. A non-transitory, computer-readable data storage medium encoded with programming instructions, said storage medium being loaded into a control computer of a magnetic resonance (MR) apparatus, said MR apparatus also comprising an MR scanner, said programming instructions causing said control computer to:
    operate said MR scanner in order to execute a localization scan of an object;
    automatically determine localization information from said localization scan that describes an arrangement of the object in the MR scanner with respect to a reference position;
    automatically execute an auto-align function algorithm in order to determine at least one item of alignment information from the localization information, with positioning information being individually assigned by a processor to a respective examination region of the object, with each item of alignment information comprising an item of positioning information for a slice in the respective examination region;
    receive at least one slice positioning entry into said control computer that includes an item of manual positioning information describing a manual positioning of the object in the MR scanner;
    automatically determine offset information dependent on said at least one slice positioning entry, said offset information including a relative slice positioning of said slice effected only by said manual positioning information, with respect to said reference position;
    automatically determine a position of the object in the MR scanner dependent on said at least one slice positioning entry and said offset information in order to operate the MR scanner to acquire MR data from the slice to place the slice at the determined position;
    operate said MR scanner in order to obtain an MR image of the slice at the determined position, and making the MR image of the slice at the determined position available in electronic from the processor, as a data file;
    electronically store the offset information separately from the determined position of the object, in a magnetic resonance measurement protocol in a form that is retrievable to automatically operate the MR scanner, using the magnetic resonance measurement protocol, to acquire said MR data from said slice;
    in a different acquisition of MR data for a different slice in the object, separately retrieve the offset information and using the retrieved offset information to set, a different slice position for said different slice in said different MR data acquisition, and operate the MR scanner to obtain an MR image of said different slice at said different slice position; and
    make said MR image of said different slice available from said processor in electronic form, as a further data file.

* * * * *